United States Patent [19]

Roman

[11] 4,324,915
[45] Apr. 13, 1982

[54] KETOENAMINE PYRETHROID INTERMEDIATES

[75] Inventor: Steven A. Roman, Oakdale, Calif.

[73] Assignee: Shell Oil Company, Houston, Tex.

[21] Appl. No.: 259,725

[22] Filed: May 1, 1981

[51] Int. Cl.³ ............... C07C 45/00; C07C 83/00; C07C 87/24
[52] U.S. Cl. ................... 564/454; 568/303; 568/351
[58] Field of Search ......................... 564/454

[56] References Cited

U.S. PATENT DOCUMENTS 3,621,060 11/1971 Selin ........................... 260/563
3,711,547 1/1973 Siddall et al. ................ 564/454
3,711,548 1/1973 Sidall et al. ................. 564/454

FOREIGN PATENT DOCUMENTS 36-6882 4/1961 Japan ........................... 564/454

OTHER PUBLICATIONS

Comi, Richard et al., Tetrahedron Letters, No. 33, pp. 3107–3109, (1973).

Primary Examiner—Paul F. Shaver

[57] ABSTRACT

Novel pyrethroid intermediates

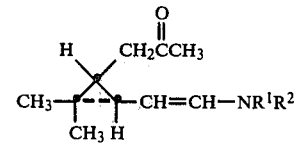

wherein $R^1$ and $R^2$ each is alkyl are prepared by treating 2,2-dimethyl-3-(2-oxopropyl)cyclopropylacetaldehyde with a trialkylsilyldialkylamine. The above compounds can be treated with ozone to form 2,2-dimethyl-3-(2-oxopropyl)cyclopropanecarbaldehyde.

7 Claims, No Drawings

KETOENAMINE PYRETHROID INTERMEDIATES

BACKGROUND OF THE INVENTION

1. Field of the Invention

This invention is directed to novel ketoenamines, their preparation and their use in processes to prepare cyclopropanecarboxylic acid pyrethroid intermediates.

2. Description of the Prior Art

U.S. Pat. Nos. 3,922,269 and 4,024,163 describe pyrethroids prepared using certain cyclopropanecarboxylic acid intermediates. The patents and literature describe various methods of preparing various pyrethroid acid intermediates, in some cases from the natural terpene, carene. For example, U.S. Pat. No. 3,565,915 illustrates a carene route to chrysanthemic acid involving the step of conversion of 2,2-dimethyl-3-(2-oxopropyl)cyclopropylacetaldehyde to the corresponding 2-acetyl-6,6-dimethyl-bicyclo[3.1.0]-2-hexane.

SUMMARY OF THE INVENTION

The present invention is directed to novel compounds of the formula

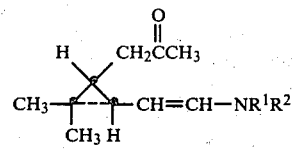

wherein $R^1$ and $R^2$ each independently is an alkyl group containing from 1 to 10 carbon atoms. Preferably, $R^1$ and $R^2$ are each an alkyl group containing from 1 to 4 carbon atoms, especially a methyl group.

The compounds of the invention may exist as geometric and/or optical isomers by virtue of the presence of unsaturation and asymmetric carbon atoms. The cis configuration of the compounds is generally preferred as the derived pyrethroid esters usually have higher pesticidal activity as compared to the cis/trans mixture. These stereo configurations are used substantially free of other stereoisomers and their purity is at least about 75% and preferably at least about 80%. Higher purities, such as at least about 95% are especially useful.

The present invention is also directed to a process for the preparation of novel pyrethroid intermediates of the formula

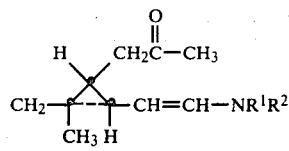

wherein $R^1$ and $R^2$ each independently is an alkyl group containing from 1 to 4 carbon atoms, which process comprises treating 2,2-dimethyl-3-(2-oxopropyl)cyclopropylacetaldehyde of the formula

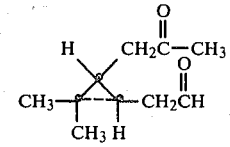

with a trialkylsilyldialkylamine, $(R^3)_3SiNR^1R^2$, in which $R^1$ and $R^2$ have the above meanings and each $R^3$ is independently an alkyl group containing from 1 to 4 carbon atoms. $R^1$ and $R^2$ are of course selected by the corresponding groups desired in the resulting product. Each $R^3$ is suitably a methyl group.

The process is conducted at atmospheric pressure and from about $-10°$ C. to about ambient temperatures. A temperature of about $-5°$ C. to about $5°$ C. is preferred.

The molar ratio of reactants is not critical. Generally, a molar ratio of aldehyde to amine is from about 1:1.1 to about 1:1.5, preferably from about 1:1.1 to about 1:1.2, and especially a molar ration of about 1:1.1.

A solvent is not required but may be used. Alkanols and amides are suitable, for example, methanol, ethanol, or dimethylformamide.

The process is conducted by adding the silylated amine to the acetaldehyde while agitating the reaction mixture, e.g., stirring, and maintaining the desired reaction temperatures. The resulting product can be purified by conventional techniques known in the art for enamines but is preferably used directly for the preparation of 2,2-dimethyl-3-(2-oxopropyl)cyclopropanecarbaldehyde as described below.

The present process is also directed to a process for the preparation of a known pyrethroid intermediate 2,2-dimethyl-3-(2-oxopropyl)cyclopropanecarbaldehyde of the formula

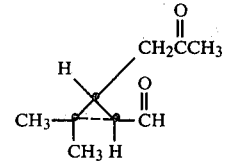

which comprises ozonolysis of a compound of the formula

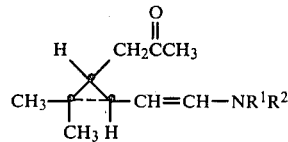

wherein $R^1$ and $R^2$ each independently is an alkyl group of from 1 to 4 carbon atoms. The ozonolysis process is conducted with ozone or with a mixture of ozone and an inert gas, such as nitrogen or argon or a mixture of ozone with oxygen or air.

The ozonolysis process is conducted at atmospheric pressure at a temperature from about $-80°$ C. to about $20°$ C., preferably from about $-80°$ C. to about $-60°$ C.

A solvent is preferably used in the ozonolysis process. The solvent used can be any solvent which will not interfere with the reaction. Suitable solvents include aliphatic hydrocarbons, cycloaliphatic hydrocarbons, aromatic hydrocarbons, halogenated hydrocarbons, dialkyl ethers or mixtures thereof. Aliphatic and cycloaliphatic hydrocarbon solvents contain from 5 to 10 carbon atoms, such as n-pentane, n-hexane, n-octane, n-heptane, n-nonane, n-decane and their isomers. Gasolines rich in alkanes are also suitable, for example, with a boiling range at atmospheric pressure of between about 40° C. to 60° C., of 60° C. to 80° C. or of 80° C. to 110° C. Petroleum ether is also suitable. Aromatic hydrocarbon solvents contain from 6 to 10 carbon atoms, such as benzene, toluene, o-, m- and p-xylene, the trimethylbenzenes, p-ethyltoluene and the like. Suitable halogenated hydrocarbons contain 1 to 4 halogen atoms, preferably chlorine atoms, in combination with an alkane chain containing from 1 to 4 carbon atoms or with a benzene ring, such as carbon tetrachloride, trichloroethane, perchloroethylene, methylene chloride, chloroform, 1,2-dichloroethane, chlorobenzene and 1,2- and 1,3-dichlorobenzene. Dialkyl ethers contain from 4 to 6 carbon atoms, for example, diethyl ether or diisopropyl ether and the like. Methylene chloride is the preferred solvent.

The ozonolysis is continued until a blue color persists. The resulting solution is purged with nitrogen or air to remove any excess ozone. The resulting product can be purified by conventional procedures known in the art but is preferably used directly to prepare known pyrethroid acids, for example, in the process described in Agri. Biol. Chem., 29(8), p. 7849 (1965), U.S. patent 3,527,769 or copending U.S. Ser. No. 153,996.

ILLUSTRATIVE EMBODIMENTS

This invention is further illustrated by the following embodiments which describe the preparation of typical species of the invention. The embodiments are presented for the purposes of illustration only and should not be regarded as limiting the invention in any way. The identity of the products, including intermediates, was confirmed by elemental, infrared and nuclear magnetic resonance spectral (NMR) analyses as necessary.

EMBODIMENT I 1-(3-(2-(Dimethylamino)ethenyl)-2,2-dimethylcyclopropyl)-2-propanone To 6.7 g of 2,2-dimethyl-3-(2-oxopropyl)cyclopropylacetaldehyde at 0° C. was added 5.2 g of trimethylsilyldimethylamine over a 5 min period. The resulting product was distilled through a spiral bantamware column to yield 6.7 g of the desired product having a boiling point of 85°–90° at 1 mm Hg.

Embodiment II 2,2-Dimethyl-3-(2-oxopropyl)cyclopropanecarbaldehyde

To a solution 2.4 g of 1-(3-(2-(dimethylamino)ethenyl)-2,2-dimethylcyclopropyl)-2-propanone, the product of Embodiment I, in 50 ml of methylene chloride was added 0.6 g of ozone over 20 min at −80° C. The resulting mixture was purged with air and 1.5 g of triethylamine was added dropwise at −30° C. The resulting mixture, after stirring and warming to room temperature, had a negative test to starch iodide paper. The reaction mixture was poured into 25 ml 1 N hydrochloride acid solution. The resulting mixture separated into two phases and the methylene chloride phase was washed with water, dried with MgSO4, filtered and stripped to yield 1.6 g of the desired product as an oil.

Embodiment III 1-(3-(2-Dimethylamino)ethenyl)-2,2-dimethylcyclopropyl)-2-propanone To 3.4 g of neat 2,2-dimethyl-3-(2-oxopropyl)cyclopropylacetaldehyde was added dropwise over 10 minutes 2.4 g of trimethylsilyldimethylamine while stirring at 0° C. The resulting mixture was pumped under vacuum to remove volatile by-products leaving 3.6 g of the desired product as a pale yellow oil. The distilled product had a boiling point of 85°–90° at 1 mm Hg, $(\alpha)_D^{30} -13.1°$ (CHCl3,c4).

I claim:

1. A compound of the formula

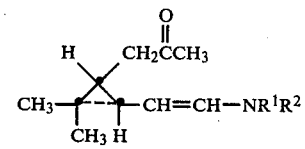

wherein $R^1$ and $R^2$ each independently is an alkyl group containing from 1 to 4 carbon atoms.

2. A compound according to claim 1 wherein $R^1$ and $R^2$ each is a methyl group.

3. A compound according to claims 1 or 2 having the cis configuration, substantially free of other stereoisomers.

4. A process for the preparation of a compound of the formula

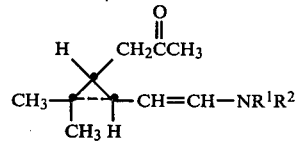

wherein $R^1$ and $R^2$ each independently is an alkyl group containing from 1 to 4 carbon atoms, which process comprises treating 2,2-dimethyl-3-(2-oxopropyl)cyclopropylacetaldehyde with a trialkylsilyldialkylamine, $(R^3)_3SiNR^1R^2$, in which $R^1$ and $R^2$ have the above meanings and each $R^3$ is independently an alkyl group containing from 1 to 4 carbon atoms.

5. A process according to claim 4 in which a trialkylsilyldialkylamine is used.

6. A process according to claim 5 wherein trimethylsilyldimethylamine is used.

7. A process according to claim 4 wherein the molar ratio of aldehyde to amine is from about 1:1.1 to about 1:1.5.

* * * * *